(12) United States Patent
Weber

(10) Patent No.: US 7,678,072 B2
(45) Date of Patent: Mar. 16, 2010

(54) AUTOMATIC INJECTION DEVICE FOR TWO-CHAMBER AMPOULES

(75) Inventor: Wilfried Weber, Schopfloch (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 26 days.

(21) Appl. No.: 12/067,766

(22) PCT Filed: Aug. 31, 2006

(86) PCT No.: PCT/DE2006/001512

§ 371 (c)(1),
(2), (4) Date: Mar. 21, 2008

(87) PCT Pub. No.: WO2007/033638

PCT Pub. Date: Mar. 29, 2007

(65) Prior Publication Data

US 2008/0188798 A1   Aug. 7, 2008

(30) Foreign Application Priority Data

Sep. 22, 2005   (DE)   .................. 20 2005 014 958 U

(51) Int. Cl.
*A61M 37/00* (2006.01)
(52) U.S. Cl. .................................. 604/82; 604/134
(58) Field of Classification Search .................. 604/82, 604/117, 131, 141, 151, 152, 157
See application file for complete search history.

(56) References Cited

U.S. PATENT DOCUMENTS

2002/0183690 A1*  12/2002  Arnisolle ..................... 604/83
2003/0105430 A1*  6/2003  Lavi et al. ..................... 604/136
2003/0171716 A1*  9/2003  Ejlersen ........................ 604/117

* cited by examiner

*Primary Examiner*—Nicholas D Lucchesi
*Assistant Examiner*—Gerald Landry, II
(74) *Attorney, Agent, or Firm*—Browdy & Neimark, PLLC

(57) ABSTRACT

An injection device for holding and activating a two-chamber ampulla has components whose relative movement causes the pistons of the two-chamber ampulla to be moved in order to mix the substances, as well as devices for injecting the product which is mixed in this way. For this purpose, a receptacle (103) into which the two-chamber ampulla (111) can be inserted and secured is held in a housing (101), and the receptacle (103) can be displaced by means of a carriage (108). A tappet (104) which acts on the pistons (111A, 111B) is movably held in the receptacle (103). A traction cable (114) which is deflected by means of a roller (109) which is mounted on the carriage (108) and one of whose ends is connected to the receptacle (103) and the other end of which is connected to a tension spring (110) which is held on the housing (101) is provided in order to carry out a mixing stroke, insertion stroke, injection stroke and a return stroke. Devices which can be activated automatically and/or manually between the housing (101), receptacle (103), tappet (104) and carriage (108) control their alternating coupling to the traction cable (114) and thus the sequence of the mixing stroke, insertion stroke, injection stroke and return stroke. The invention thus provides a partially automatic injection device for two-chamber ampullas whose handling comfort and safety for the patient are substantially improved.

18 Claims, 7 Drawing Sheets

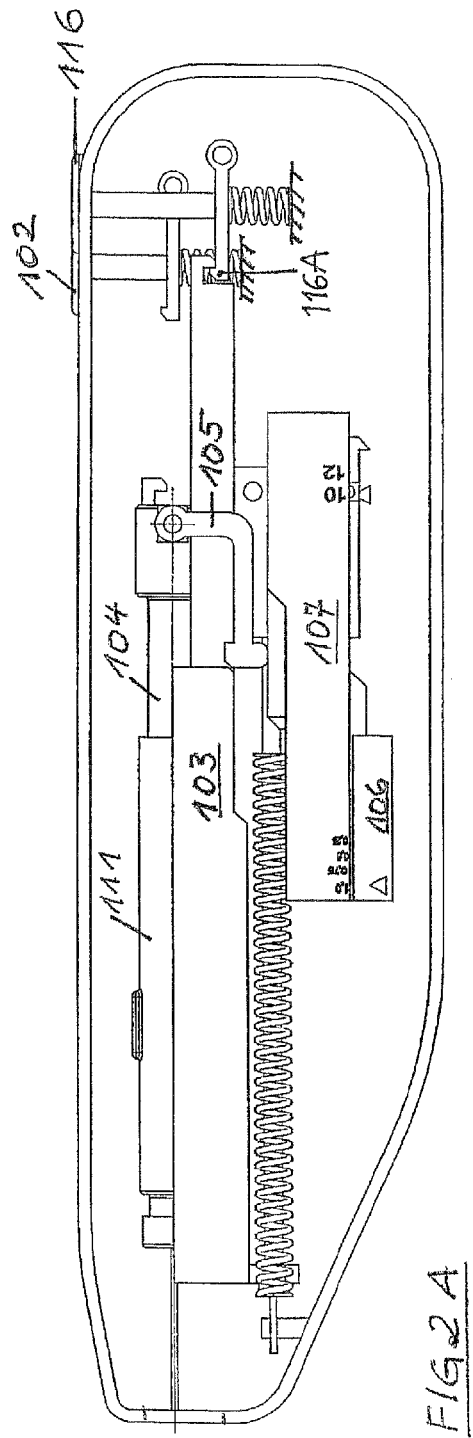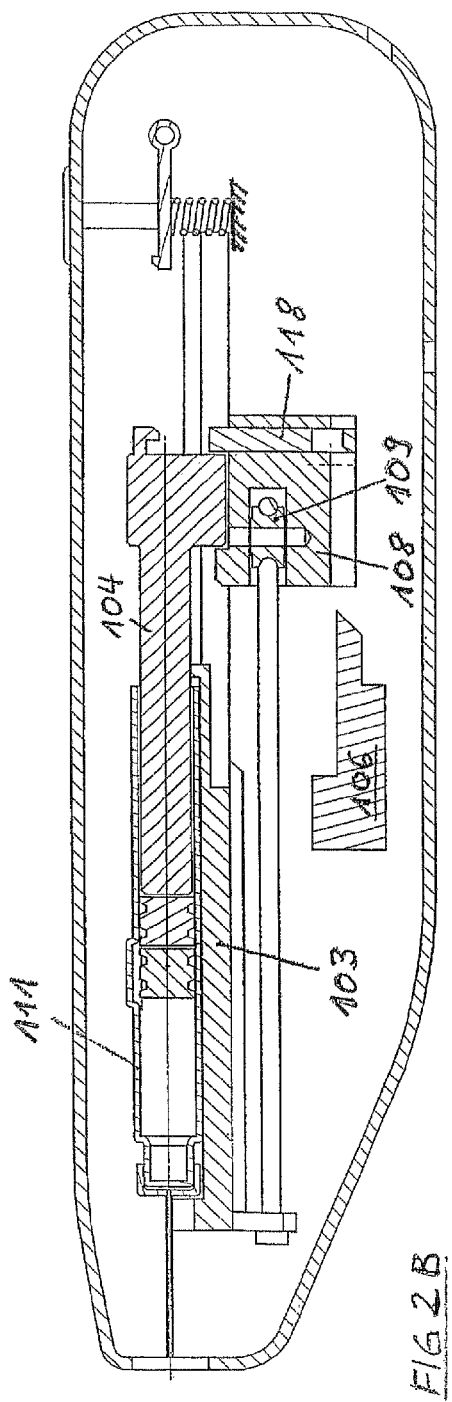
FIG 2A
FIG 2B

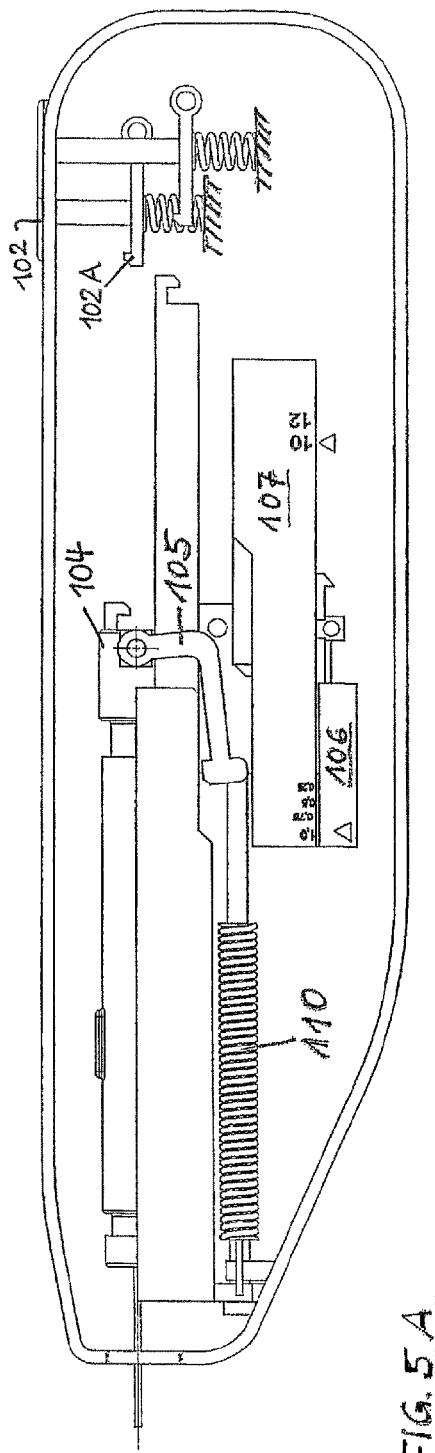
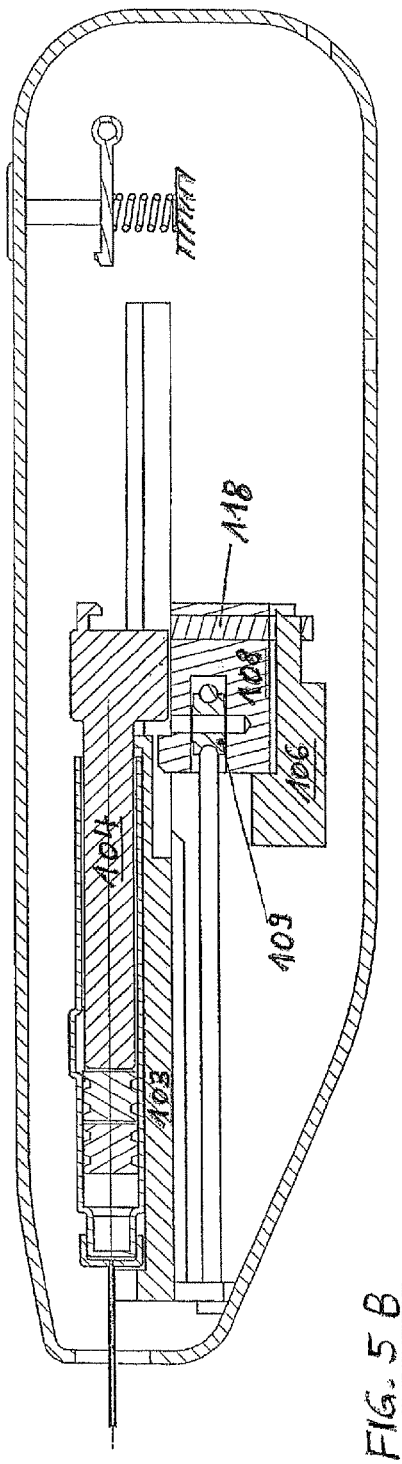
FIG. 5A
FIG. 5B

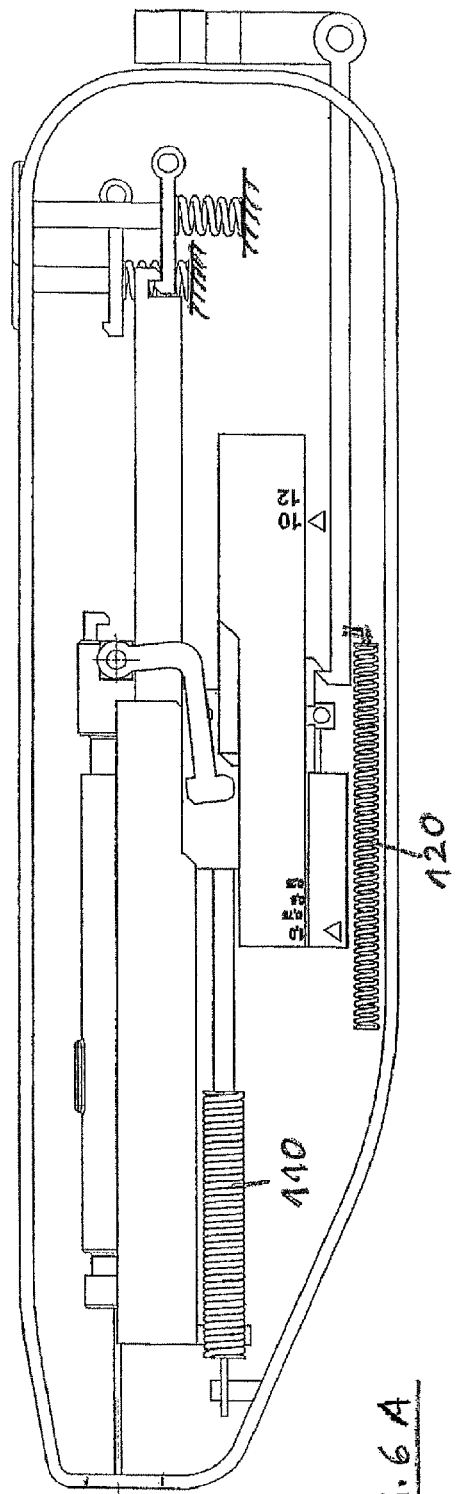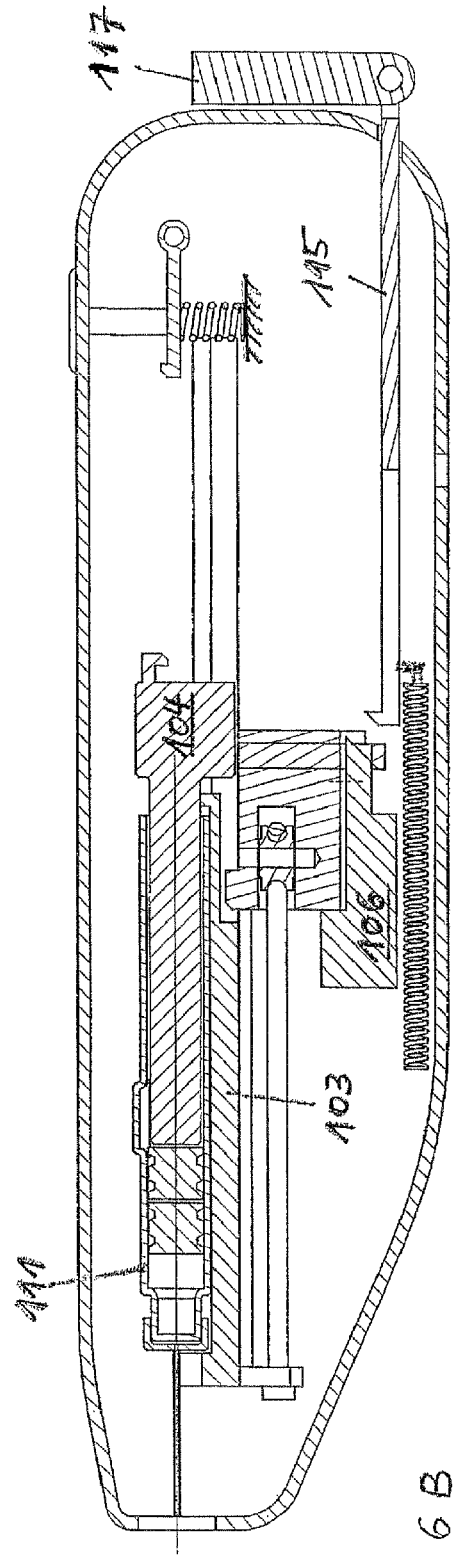
FIG. 6A
FIG. 6B

AUTOMATIC INJECTION DEVICE FOR TWO-CHAMBER AMPOULES

For the treatment of a multitude of illnesses, such as diabetes, which are now widespread, patients must inject themselves independently with the needed amount of an active substance/medicament, using a syringe or a carpule. To make this safer and easier, a multitude of injection devices are known that incorporate a largely automatic sequence of inserting the needle, injecting the active substance and withdrawing the needle.

PRIOR ART

For the use of disposable hypodermic syringes, a number of devices are known for an automatic injection of the active substance that is contained in the syringe; WO 2005/011780 or WO 99/56805, for instance, reveal injection devices that permit a fully automatic sequence of the above-described processes while being simple to operate.

In recent times it has become apparent that an improvement of the treatment result, or ensuring a medical success to begin with, requires the use of active substances that need to be mixed with another active substance immediately prior to being injected; one example for this is Betaferon for mixing with a NaCl solution. To achieve this goal, the two active substances, as a rule, are contained inside a syringe body with two chambers, which are separated from each other and between which an interconnection, through which the two active substances are then intermixed (visible for the patient, if possible), is created only shortly prior to the injection.

For these special syringe bodies, which will be referred to below as two-chamber ampoules, injection devices are known, with the aid of which a process sequence of mixing, inserting and injecting is made possible (DE 600 11 853 T2). Controlling these process sequences takes place manually, however, and handling accordingly requires great attention on the part of the patient, especially also since no provision is made for a withdrawal of the needle after the completed injection.

A delivery device for a multi-chamber ampoule is revealed in DE 103 40 585 A1. The manual effort that is required for the injection is similar here, two cylindrical housing halves that are disposed coaxial relative to each other, into which the ampoule has been inserted, are manually compressed or screwed together for mixing until an end position is reached; afterwards the injection is to be performed by means of a "delivery mechanism", which is not revealed in detail. Here again, no provision is made for an automatic withdrawal of the needle.

DISCLOSURE OF THE INVENTION

It is the object of the invention to improve an injection device for a two-chamber ampoule through automatization of the sequences in such a way that the handling comfort and safety for the patient are improved, while providing for a simple mechanical design.

It is an additional object of the invention to individually regulate the dosages for each patient, which are relatively critical in the case of two-component substances, and also the associated insertion depths at the injection site, so that an optimization can be attained for each patient both with regard to the injected volume of the active substance, as well as with regard to the insertion depth of the needle.

The inventive injection device meets this object with the characteristics of claim 1.

The underlying inventive idea lies in effecting the sequence of the strokes solely by means of a simple drive mechanism, namely a traction-cable system. To this effect, the stroke that is carried out by the tappet upon activation of the two-chamber ampoule, is divided into a preceding mixing stroke and an injection stroke, which are interrupted by the insertion stroke. This ensures that the insertion of the needle into the injection site takes place only after mixing of the two active substances has occurred and was optionally assessed as correct by the patient through a window.

Preferred embodiments relate to the design of the adjusting elements for controlling the process sequence, which are designed also to provide for independent adjustments of the insertion depth and of the injection volume of the mixed active substance.

Additional embodiment designs are specified in additional subclaims.

BRIEF DESCRIPTION OF THE DRAWINGS

A preferred exemplary embodiment of the injection device will now be explained with the aid of drawings, in which FIG. 2A shows a side view of the injection device during the performance of the mixing stroke, FIG. 2B shows a sectional view corresponding to FIG. 2A, FIG. 5A shows a side view of the injection device at the start of the needle withdrawal, FIG. 5B shows a sectional view according to FIG. 5A, FIG. 6A shows a side view of the injection device after completion of the needle withdrawal, and FIG. 6B shows a sectional view according to FIG. 6A,

DESCRIPTION OF THE EXEMPLARY EMBODIMENT

To inject the active substance, a two-chamber ampoule 111 is used. An ampoule of this type (FIG. 1B) has two pistons 111A, 111B, resulting in two initially independent chambers 111C, 111D. Into the first, inner chamber 111C, which faces the needle 112, powdered Betaferon is filled, for example, and into the second, outer chamber 111D, a NaCl solution is filled.

If a tappet 104 is now pressed against the outer piston 111B, the inner piston 111A is initially displaced as well, since the NaCl solution hydraulically transfers the force of the tappet onto the inner piston 111A. As soon as the inner piston 111A has passed an overflow channel 111E in the form of a groove-like convexity in the outer wall of the ampoule 111, it comes to a standstill and the NaCl solution flows through this overflow channel 111E into the inner chamber 111C and mixes with the Betaferon. After the mixing process, the injection then takes place (after the insertion stroke) through the continued movement of the tappet 104.

Figure 1A:
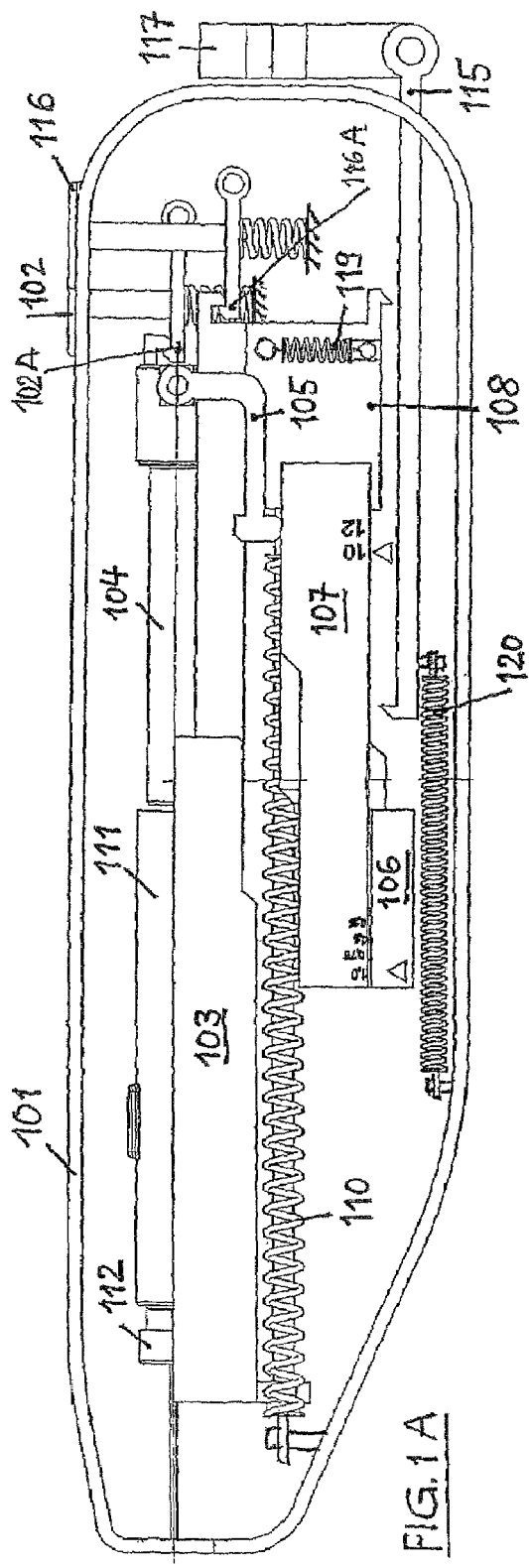
FIG. 1A shows a side view of the injection device in the starting position.
Figure 1B:
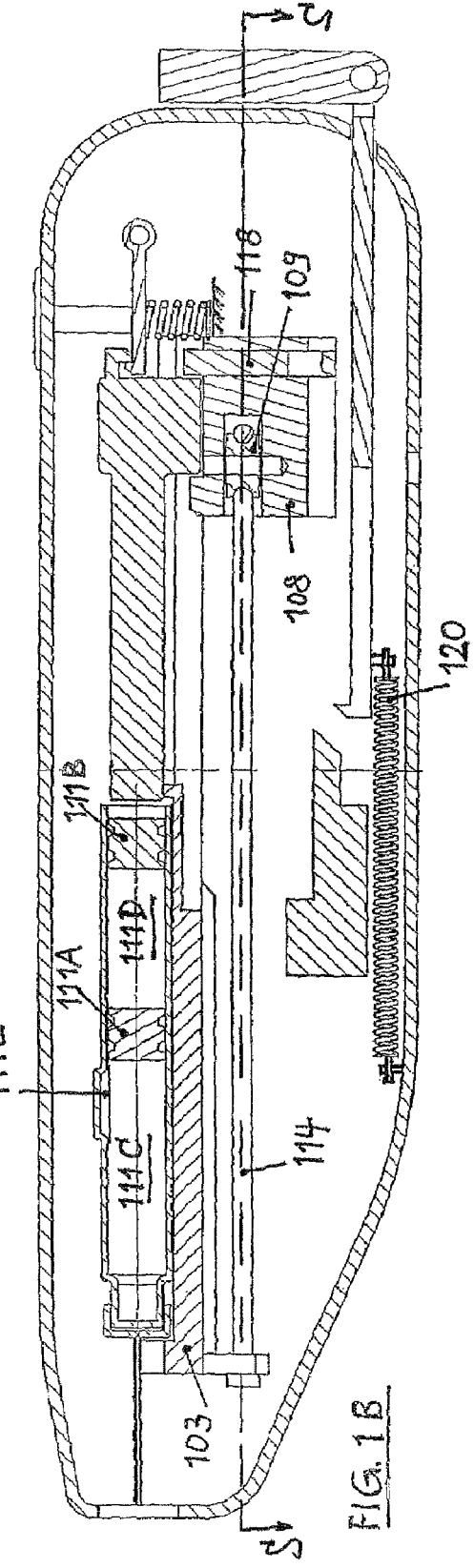
FIG. 1B shows a section through the injection device of FIG. 1 in its initial position in its center plane.
Figure 1C:
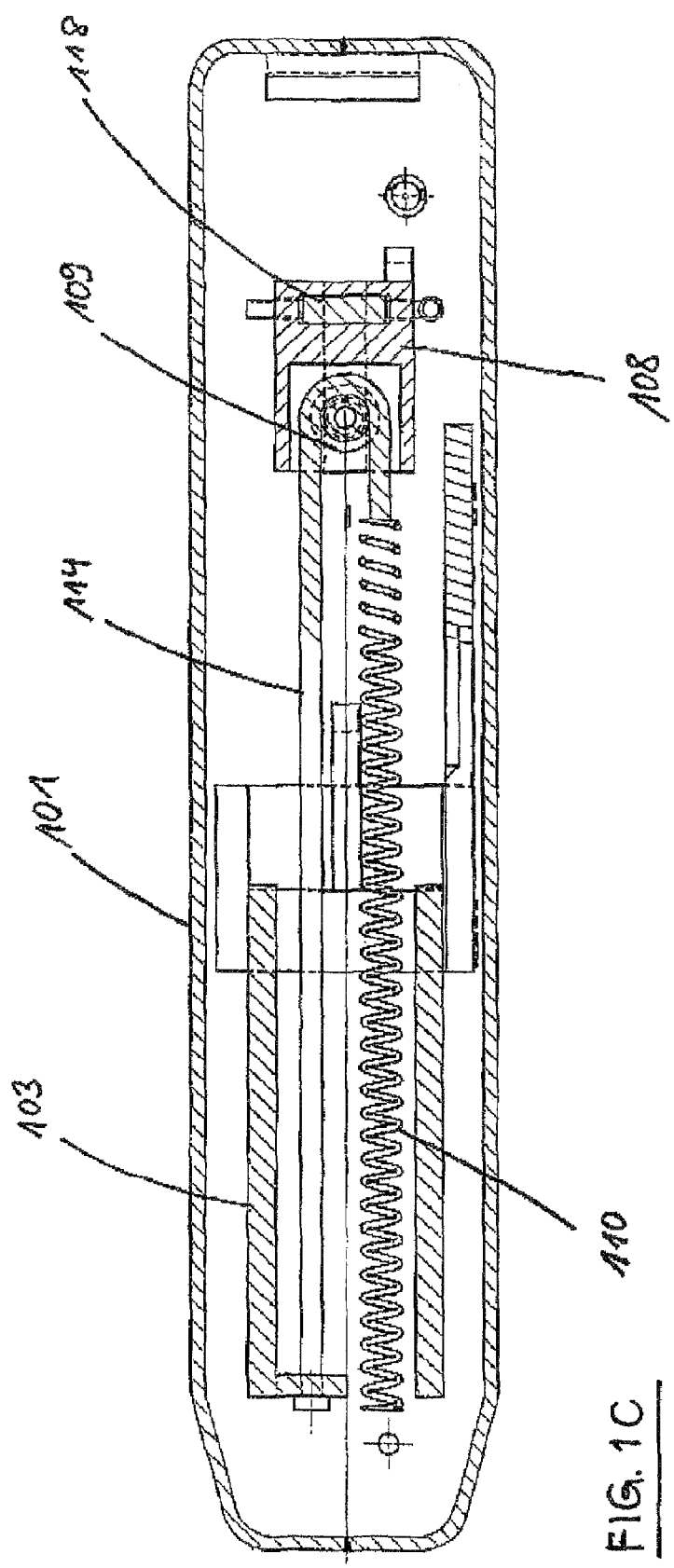
FIG. 1C shows a section through the injection device in the plane S-S of FIG. 1B.

FIG. 1A shows a top view, FIG. 1B shows a sectional view in the starting position of the injection device, FIG. 1C shows an additional section in the plane S-S.

All components are situated inside a housing 101 composed of two tub-shaped half-shells. The movable components are held inside the injection device so as to be displaceable parallel to the longitudinal axis of the needle. The components are assigned to each other as follows:

A two-chamber ampoule 111 is held in a receptacle 103. A tappet 104, to the rearward end of which a control lever 105 is hinged, is held on a locking hook 102A of a spring-actuated first push-button 102. The receptacle 103 is held on a locking hook 116A of a spring-actuated second push-button 116.

Acting on the receptacle 103 is the end of a traction cable 114, which is deflected by means of a roller 109, which is mounted in a cradle 108 and connected to a tension spring 110, which is fixed to the housing 101. The tension spring 110 thus exerts a pull on the receptacle 103 in the direction away from the injection site. The receptacle 103 cannot slide in the axial direction, however, because it is held by the locking hook 116A on the second push-button 116.

The deflection of the traction cable 114 via the roller 109 creates a force on the cradle 108 in the direction toward the injection site. The cradle 108 remains it its position, however, because it rests against the tappet 104 via a driving feature 118, which is mounted in the cradle 108 so as to be displaceable perpendicular to the injection device and which is actuated by a driving-feature spring 119, and the tappet 104 is held by the locking hook 102A on the first push-button 102.

Assigned to the control lever 105 is a first adjusting slider 107, in which a second adjusting slider 106 is supported so as to be displaceable. The adjusting slider 106 provides for the uncoupling of the cradle 108 from the tappet 104. The adjusting sliders 106, 107 are designed as displaceably mounted end-stop elements for adjusting the insertion depth and injection volume, as will be explained further below.

A pull-back handle 117, which is connected to a tension rod 115, serves to create this starting position. The tension rod 115 is actuated by a pull-back spring 120.

Description of the Process

When the first push-button 102 is actuated, this causes the locking hook 102A to move out of engagement, the tappet 104 is released and moves toward the injection site, until the front edge of the control lever 105 comes to rest against the receptacle 103. In this manner the outer piston 111B of the ampoule 111 is activated, moves forward and carries out a mixing stroke H0. This mixing stroke serves for mixing of the NaCl solution with the Betaferon, as described above (FIG. 2A, FIG. 2B). A window in the housing 101 makes it possible to monitor the mixing of the Betaferon with the NaCl solution.

Since the free end of the control lever 105, on the other hand, slides on the second adjusting slider 107 and rests on it, it cannot yield in a downward direction by pivoting at this location; the pulling force of the tension spring 110 toward the injection site is therefore transferred from the cradle 108 via the tappet 104 to the receptacle 103. The receptacle 103 remains in its position, however, because it is locked in place by the locking hook 116A of the push-button 116.

Figure 3A:
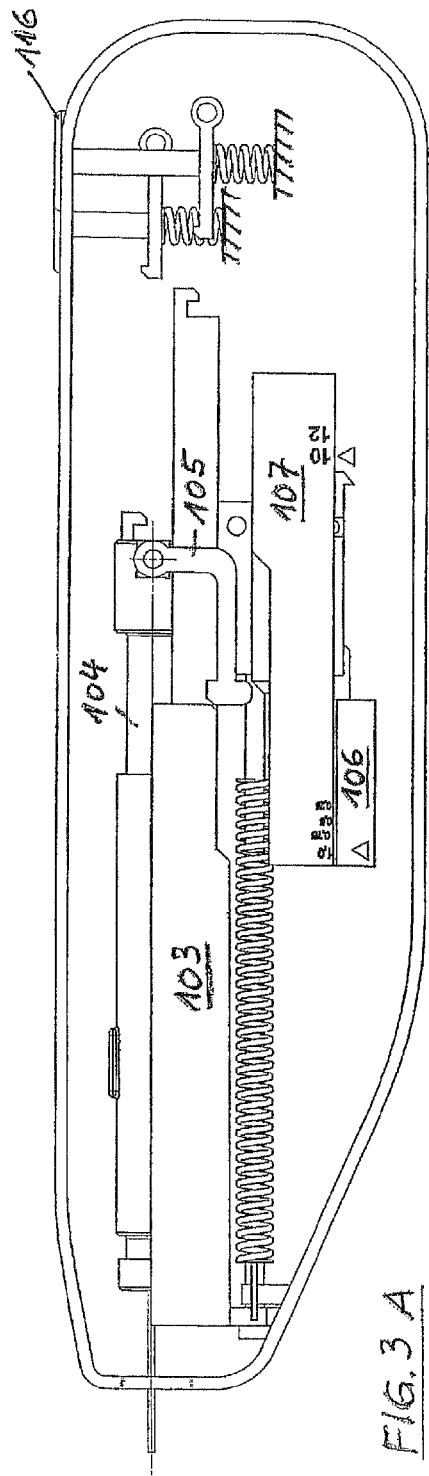
FIG. 3A shows a side view of the injection device during the injection stroke.
Figure 3B:
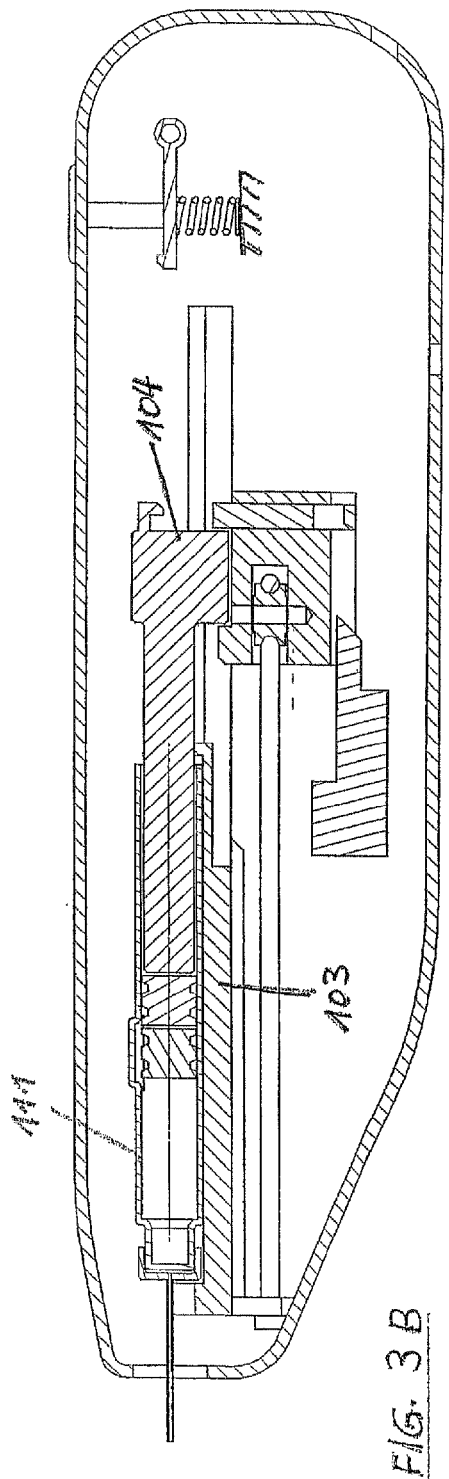
FIG. 3B shows a sectional view according to FIG. 3A.
Figure 4A:
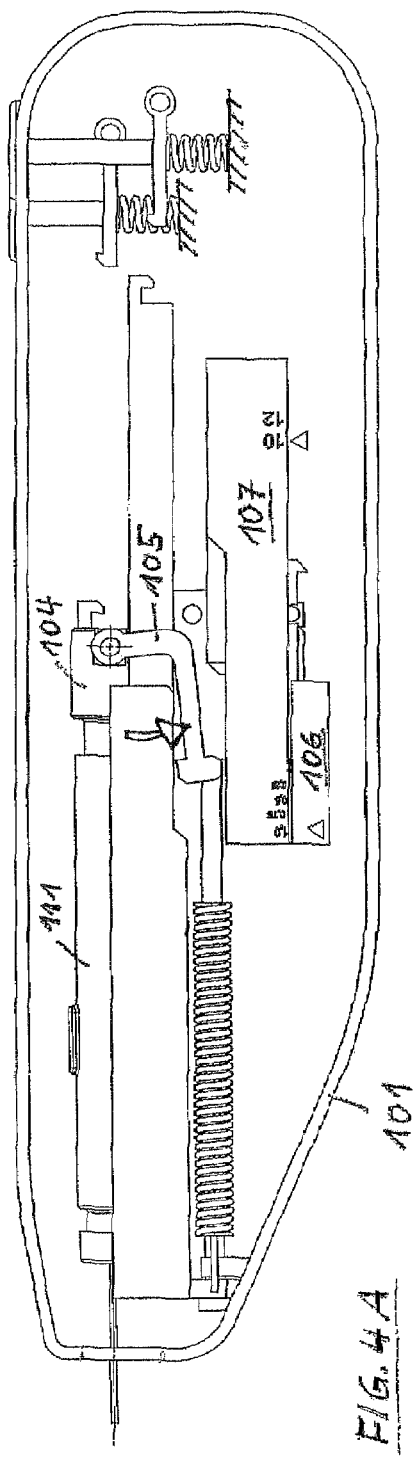
FIG. 4A shows a side view of the injection device during the injection stroke.
Figure 4B:
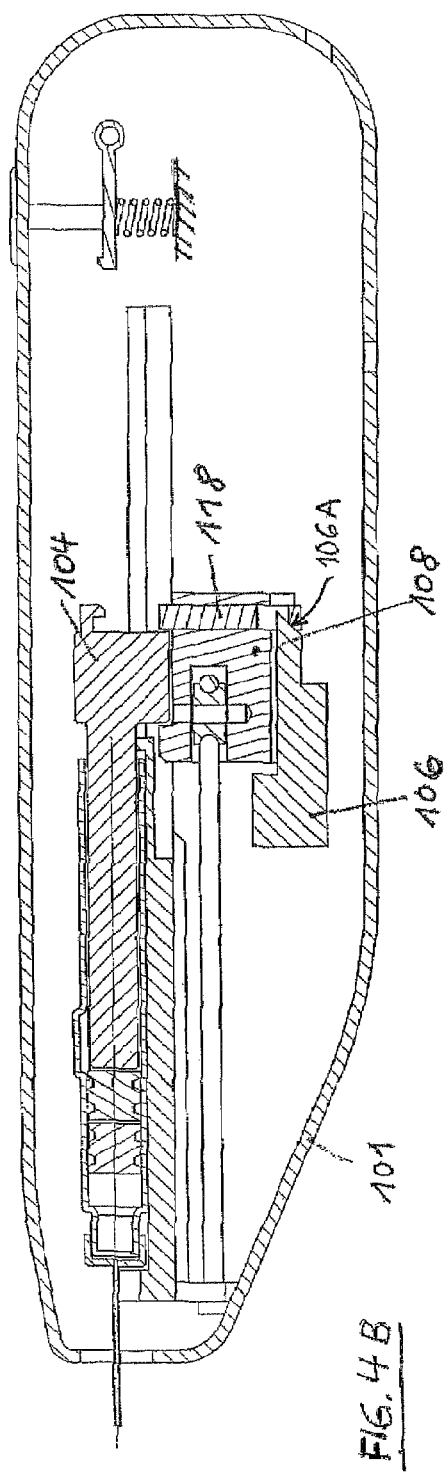
FIG. 4B shows a sectional view according to FIG. 4A.

When the second push-button 116 is now actuated, this causes the locking hook 116A to move out of engagement and the receptacle 103 is released; this causes the tappet 104 and the receptacle 103 to jointly move toward the injection site under the action of the tension spring 110. The needle is inserted (FIG. 3A, 3B), the injection stroke H1 is carried out (FIG. 4A, 4B.)

Once the desired insertion depth is reached, the control lever 105 is able to pivot downward (arrow in FIG. 4A), since it is no longer prevented from doing so by the first adjusting slider 107 due to its recessed upper surface. Consequently, force is no longer transferred from the tappet 104 to the receptacle 103, the receptacle 103 remains in its position, and only the tappet 104 continues to move toward the injection site, i.e., injection of the medication takes place, the injection stroke H2 is carried out.

Once the driving feature 118, which is mounted in the cradle 108 so as to be able to slide, reaches the ramp 106A of the second adjusting slider 106 (FIG. 4B), the driving feature 118 is pulled downward and the cradle 108 is thus uncoupled from the tappet 104, i.e., at this point in time the injection is terminated (FIG. 5B).

The cradle 108 now rests against the adjusting slider 106. Since the adjusting slider 106 is held form-fittingly on the housing 101 by means of the first adjusting slider 107, the pulling force of the tension spring 110 (which is fixed to the housing 101) now acts via the roller 109 on the receptacle 103, causing the same to be pulled back, and consequently causing the needle to be pulled out of the injection site (FIG. 6A, 6B), the return stroke H3 is carried out.

By folding down the pull-back handle 117, which is connected to the tension rod 115, and pulling out the tension rod 115, the cradle 108 and all other elements are pulled back into their starting position (FIG. 1A, 1B). The tension rod 115 is retracted into its initial position by the pull-back spring 120.

The ampoule can now be removed.

The injection volume and insertion depth can be adjusted as follows:

The first adjusting slider 107 is mounted in the housing 101 so as to be axially displaceable, in the present example it has 2 locking positions (10 and 12 mm, set to 10 mm in the example). These locking positions are assigned to the injection stroke H1, since the axial position of the adjusting slider 107 determines the path until the control ever 105 uncouples the tappet 104 from the receptacle 103 (FIG. 2A).

In the first adjusting slider 107, the second adjusting slider 106 is mounted so as to be axially displaceable as well, in the present example with 4 locking positions (1.0; 0.75; 0.5; 0.25, set to 1.0 in the example). These locking positions are assigned to the injection stroke H2, since the axial position of the adjusting lever 106 determines the path until the tappet 104 is uncoupled from the cradle 108 (FIG. 5A, 5B), and withdrawal of the needle takes place.

If an insertion depth of 12 mm, for example, is now to be set, the first adjusting slider 107 must be moved by 2 mm toward the injection site, relative to the depicted state, to the new locking position on the housing 101. Since the second adjusting slider 106 is interlocked in position 1.0 with the first adjusting slider 107, it now also moves by 2 mm toward the injection site, i.e., setting a different insertion depth has no impact on the injection volume. Likewise, adjusting the injection volume has no impact on the insertion depth; the settings of the insertion stroke H1 and injection stroke H2 are independent from each other.

REFERENCE NUMERALS housing 101
first push-button 102
locking hook 102A
receptacle 103 tappet 104
control lever 105
first adjusting slider 107
second adjusting slider 106
ramp 106A
carriage 108
roller 109
spring 110
ampoule 111
hypodermic needle 112
traction cable 114
tension rod 115
second push-button 116
locking hook 116A
pull-back handle 117
driving feature 118
driving-feature spring 119
pull-back spring 120

What is claimed is:

1. An injection device for holding and activating a two-chamber ampoule provided with pistons and an overflow channel, incorporating an injection needle and incorporating components whose relative movement causes the pistons of the two-chamber ampoule (111) to be displaced in order to mix the substances until the inner piston (111A) reaches the overflow channel (111E) of the two-chamber ampoule and comes to a standstill, whereupon the outer piston (111B) transports the first active substance, which is contained in the rear chamber (111D), into the front chamber (111C) leading to the injection needle and containing the second active substance, and also incorporating devices for injecting the product that has been mixed in this way, characterized in that a receptacle (103), into which the two-chamber ampoule (111) is insertable and in which it is securable is held in a housing (101), that the receptacle (103) is displaceable by means of a cradle (108), that a tappet (104), which actuates the pistons (111A, 111B) is held displaceable in the receptacle (103), and that for performing the mixing stroke, needle-insertion stroke, injection stroke, and a return stroke, a traction cable (114) is provided, which is deflected by means of a roller (109), which is mounted on the cradle (108), and one of whose ends is connected to the receptacle (103) and the other end of which is connected to a tension spring (110), which is held on the housing (101) wherein devices, which are activated automatically and/or manually between the housing (101), receptacle (103), tappet (104) and cradle (108), control their alternating coupling to the traction cable (114) and thus the sequence of the mixing stroke, insertion stroke, injection stroke and return stroke.

2. An injection device according to claim 1, characterized in that first devices are provided for releasably locking the tappet (104) in place in order to initiate the mixing stroke.

3. An injection device according to claim 2, characterized in that the first devices comprise a locking hook (102A) of a spring-actuated first push-button (102) provided on the housing (101), wherein the locking hook (102A) acts on the tappet (104).

4. An injection device according to claim 1, characterized in that second devices are provided for releasably locking the receptacle (103) in place in order to initiate the insertion stroke following the mixing stroke.

5. An injection device according to claim 4, characterized in that the second devices comprise a locking hook (116A) on at least one spring-actuated push-button (116) provided on the housing (101), wherein the locking hook (116A) acts on the receptacle (103).

6. An injection device according to claim 1, characterized in that the traction cable (114) pulls the receptacle (103) with the ampoule and injection needle out of the injection site by means of the cradle (108) and roller (109) during the return stroke following the injection stroke.

7. An injection device according to claim 1, characterized in that third devices are provided for coupling the tappet (104) to the receptacle (103), which couple the tappet (104) to the receptacle (103) in order to carry out the insertion stroke and uncouple it in order to carry out the injection stroke.

8. An injection device according to claim 7, characterized in that the third devices comprise a control lever (105), whose one end is hinged to the tappet (104) and whose other end actuates the receptacle (103).

9. An injection device according to claim 1, characterized in that fourth devices are provided for coupling the cradle (108) and tappet (104), which couple the cradle (108) and tappet (104) from the start of the mixing stroke until the end of the injection stroke.

10. An injection device according to claim 9, characterized in that the fourth devices comprise a spring-actuated driving feature (118), which is mounted in the cradle (108) and which, in its coupled position, acts on the tappet (104).

11. An injection device according to claim 1, characterized in that it incorporates a first adjusting slider (107), which effects a setting of the path of the insertion stroke and, therefore, of the insertion depth.

12. An injection device according to claim 8, characterized in that it incorporates a first adjusting slider (107), which effects a setting of the path of the insertion stroke and, therefore, of the insertion depth, and in that the first adjusting slider (107) is designed as an end-stop element, which is mounted so as to be displaceable between two end positions as desired, and whose position determines, via the control lever (105), the path of the receptacle (103) and thus the length of the insertion stroke.

13. An injection device according to claim 1, characterized in that it incorporates a second adjusting slider (106), which effects, via the path of the tappet (104), a setting of the length of the injection stroke and thus of the injection amount of the mixed substance.

14. An injection device according to claim 13, characterized in that the second adjusting slider (106) is designed as an end-stop element for the receptacle (103), said end-stop element being mounted so as to be displaceable relative to the first adjusting slider (107) between at least two positions.

15. An injection device according to claim 11, characterized in that it incorporates a second adjusting slider (106), which effects, via the path of the tappet (104), a setting of the length of the injection stroke and thus of the injection amount of the mixed substance, and in that one of the adjusting sliders is mounted, slideable or rotatable, directly or indirectly in the respective other adjusting slider, so that the insertion depth and injection volume are adjustable independently from each other.

16. An injection device according to claim 1, characterized in that the housing (101) is composed of two half shells.

17. An injection device according to claim 16, characterized in that at least one of the half shells has a window for monitoring the mixing of the two substances in the front chamber during the mixing stroke.

18. the injection device according to claim 1, wherein said roller has an outer periphery around which said traction cable extends.

* * * * *